(12) United States Patent
Mimoun

(10) Patent No.: US 6,548,690 B2
(45) Date of Patent: Apr. 15, 2003

(54) POROUS POLYMETHYLSILSESQUIOXANE WITH ADSORBENT PROPERTIES

(75) Inventor: Hubert Mimoun, Challex (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/875,334

(22) Filed: Jun. 6, 2001

(65) Prior Publication Data

US 2002/0010300 A1 Jan. 24, 2002

Related U.S. Application Data

(63) Continuation of application No. PCT/IB99/02019, filed on Dec. 16, 1999.

(30) Foreign Application Priority Data

Dec. 22, 1998 (CH) .............................. 2533/98

(51) Int. Cl.$^7$ .............................. C07F 7/08
(52) U.S. Cl. ..................... 556/453; 556/456
(58) Field of Search ................. 556/453, 456

(56) References Cited

U.S. PATENT DOCUMENTS 5,321,102 A * 6/1994 Loy et al. ............ 556/453 UX
5,831,133 A   11/1998 Mimoun ................ 568/814
6,399,210 B1 * 6/2002 Zhong ................. 556/453 UX

FOREIGN PATENT DOCUMENTS

| EP | 0 239 795 | 12/1988 |
| EP | 0 406 911 | 1/1991 |
| JP | 06157759 | 6/1994 |
| WO | WO 96/12694 | 5/1996 |

* cited by examiner

*Primary Examiner*—Paul F. Shaver
(74) *Attorney, Agent, or Firm*—Winston & Strawn

(57) ABSTRACT

The present application describes a porous polymethylsilsesquioxane (PMS) having a specific surface area between approximately 50 m$^2$/g and 500 m$^2$/g, a pore volume between approximately 0.1 cm$^3$/g and 0.8 cm$^3$/g, a monolayer volume between approximately 10 cm$^3$/g and 60 cm$^3$/g, a pore radius smaller than 1 nm for 90% of the pores and insolubility in water and organic solvents.

The PMS according to the invention is prepared by precipitation of a polymethylsiliconate of the general formula

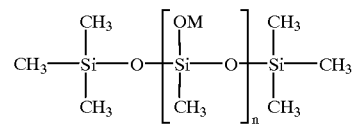

(I)

in which n is a whole number between approximately 20 and 100 and M is an alkaline metal or alkaline-earth metal or NH$_4^+$.

21 Claims, 1 Drawing Sheet

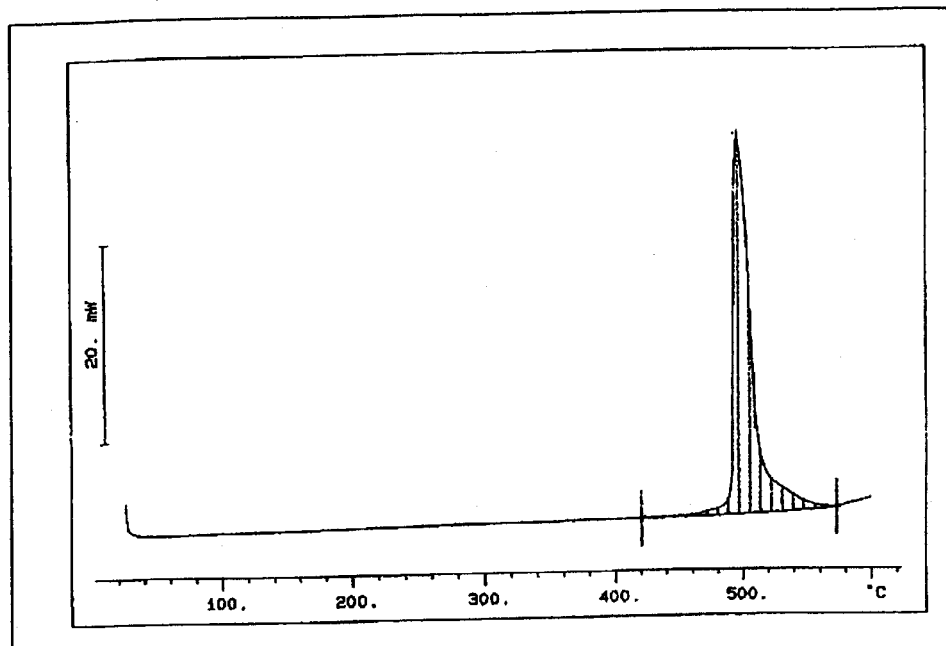
Fig. 1 Differential thermic analysis of a PMS
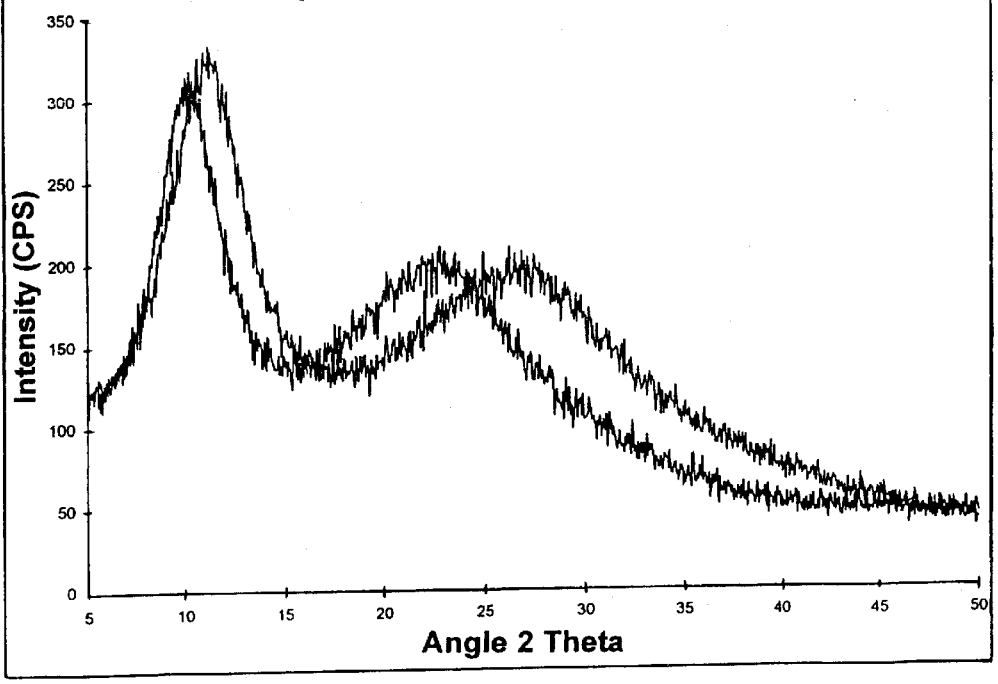
Fig. 2 X-Ray diffraction spectra of 2 qualities of porous PMS

POROUS POLYMETHYLSILSESQUIOXANE WITH ADSORBENT PROPERTIES

This application is a continuation of PCT/IB99/02019, filed Dec. 16, 1999.

TECHNICAL FIELD

The present application relates to the field of materials. More particularly, it relates to a porous, hydrophobic polymethyl-silsesquioxane having remarkable properties of adsorption of organic molecules.

PRIOR ART

The use in industry of adsorbent materials such as activated carbons, silicas, aluminas or zeolites is known for applications as varied as the purification of water or air to prevent pollution, the separation of liquids or gases by chromatography, the supporting of catalysts or the encapsulation of active substances, to quote just a few examples.

The adsorbent properties of the materials depend on a certain number of physical parameters such as apparent density, specific surface area, particle size, pore volume and pore distribution, indicating their microporosity (<2 nm), their mesoporosity (between 2 nm and 50 nm) or their macroporosity (>50 nm). A support will also be characterised by its thermal stability, its regenerability, the reversibility of its adsorbent capacities, its hydrophobicity, its inflammability and its absence of toxicity.

At present, the most commonly used hydrophobic adsorbent is activated carbon. However, this has the disadvantage of being inflammable and forming explosive mixtures with air. It is also difficult to regenerate and has a limited adsorption capacity.

Another class of commonly used adsorbents are the silicas. They exist in a wide range of specific surface areas and particle sizes and, as a result, have varying adsorbent properties.

SUMMARY OF THE INVENTION

The present application relates to a hydrophobic material which belongs to the family of polymethylsilsesquioxanes, hereinafter abbreviated to PMS, which is thermally stable and has the capacity to adsorb several times its own weight in organic substance.

More precisely, the present application describes a porous polymethylsilsesquioxane in powdered form containing the units

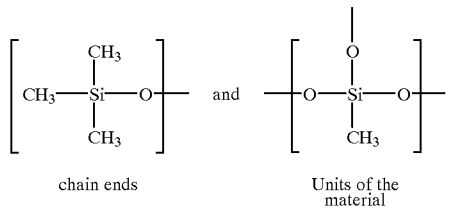

chain ends      Units of the material characterised by a specific surface area between approximately 50 m²/g and 500 m²/g, a pore radius smaller than 1 nm for 90% of the pores, and insolubility in water and organic solvents.

In preferred embodiments, the polymethylsilsesquioxane according to the invention has a pore volume between 0.1 cm³/g and 0.8 cm³/g and/or a monolayer volume between approximately 10 cm³/g and 60 cm³/g.

The polymethylsilsesquioxane according to the invention may also contain the units

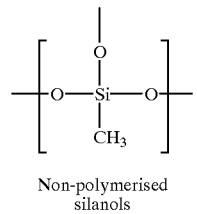

Non-polymerised silanols

They can be present owing to incomplete polymerisation during the preparation reaction described hereinbelow or owing to treatment which results in partial hydrolysis of the PMS.

The present invention also relates to a process for the preparation of the said polymethylsilsesquioxane.

BRIEF DESCRIPTION OF THE DRAWINGS

FIG. 1 is a graph of the differential thermic analysis of a MPMS according to the invention; and FIG. 2 is a graph of X-ray diffraction spectra for 2 qualities of porous PMS according to the invention.

DETAILED DESCRIPTION OF THE PREFERRED EMBODIMENTS

The polymethylsilsesquioxanes according to the invention are obtained by acid precipitation of an aqueous solution of a polymethyl-siliconate, followed by filtration and drying. The reaction for preparation of the polymethylsilsesquioxanes according to the invention is illustrated hereinbelow in the schematic equation (1), in which the formula (I) is representative of a polymethylsiliconate suitable for use in the invention and the formula (II) is representative of a precipitate forming after the addition of a suitable acid by means of a condensation reaction of the polymethylsiliconate.

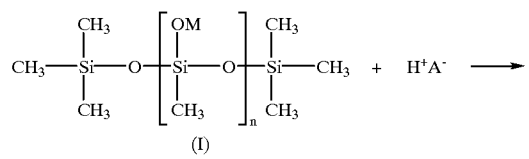

(I)

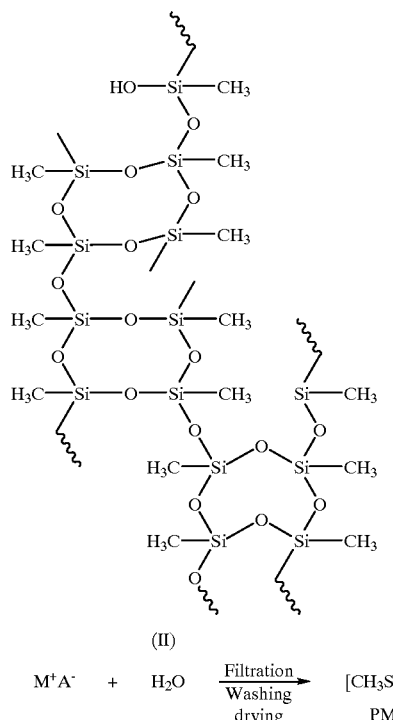

(II)

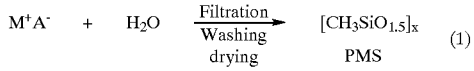

M = alkaline/alkaline-earth metal, $NH_4^+$; n = whole number from 20 to 100

The polymethylsilsesquioxane obtained by the reaction schematically shown above and forming the subject of the invention can be approximately described by the empirical formula $(CH_3SiO_{1.5})_x$. However, it is not possible to specify the value x, that is to say to give the exact molecular weight of the polymethylsilsesquioxane, given that the latter is insoluble in all known solvents in view of its very high molecular weight.

In the equation (1), the letter M represents an alkaline metal such as Li, Na, K, an alkaline-earth metal such as Mg, Ca, or an $NH_4^+$ group, preference being for Na and K. The value n in the formula (I), which represents the number of repeated $[MOSi(O)CH_3]$ units, is a whole number between 20 and 100, preferably between 30 and 80. The siliconates characterised by the formula (I) are soluble in water and can be bought on the market as aqueous solutions. We have found that good results are obtained if the product known by the name of Rhodorsil® Siliconate 51T, marketed by Rhône-Poulenc, is used as the siliconate. This product is an aqueous solution of potassium polymethylsiliconate at about 46% by weight, with a pH of about 13 and a density of about 1.34.

Nevertheless, it is also possible to prepare the polymethyl-siliconates used in the synthesis of the PMS from the polymethylhydro-siloxane known by the name of PMHS and represented by the following formula (III):

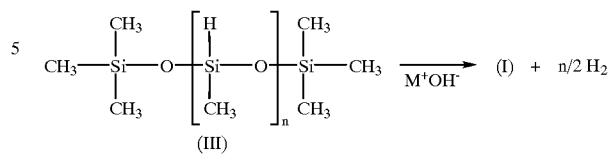

In this formula (III), n has the same value as specified hereinabove for the polymethylsiliconates, namely between approximately 20 and 100, preferably between approximately 30 and 80. The desired polymethylsiliconates are obtained by converting the Si—H bond to an Si—O⁺M⁻ bond, M representing an alkaline metal, an alkaline-earth metal or $NH_4^+$. This conversion can be carried out e.g. by alkaline hydrolysis using a base such as NaOH, KOH, $Ca(OH)_2$, or by the action of an alcohol followed by alkaline hydrolysis. It is also possible to use the polymethylsiliconates obtained by the reduction of a carbonyl substrate using PMHS and a catalyst, being a metal salt, preferably zinc, followed by alkaline hydrolysis. Such a process forms the subject of international application WO 96/12694 in the name of Firmenich SA. The content of this application in respect of the preparation of the polymethyl-siliconates from PMHS forms part of the present application and is incorporated herein by reference.

In the preparation of the said polymethylsiliconates, used as starting materials, we obtained the best results, from the point of view of the properties of the PMS obtained as end product, when we had recourse to a PMHS with a viscosity between 15 cSt and 50 cSt, preferably between 25 cSt and 35 cSt, and a density between 0.95 and 1.02.

As is evident from the equation (1), the polymethylsiliconates (I) undergo a condensation reaction when they are neutralised by a suitable acid. The acid is added until a pH of about at least 11, preferably about 7 is reached. The acid can even be added until a pH of about 1 is reached. The acid used can be a mineral acid such as sulphuric acid, phosphoric acid, nitric acid, hydrochloric acid, hydrobroic acid, hydrofluoric acid, perchloric acid or fluoroboric acid. The acid can also be an organic acid such as acetic acid, propionic acid, butyric acid, valeric acid, 2-ethylhexanoic acid, chloroacetic acid, dichloroacetic acid or trichloroacetic acid. Carbon dioxide gas can also be used.

The preferred acids are acetic acid, sulphuric acid or phosphoric acid, the latter being the most advantageous acid according to the invention.

Next, the precipitate formed during neutralisation of the polymethylsiliconate is filtered or centrifuged, then washed one or more times with water to remove the alkaline salts and, if necessary, with a solvent miscible with water, such as methanol, ethanol, isopropanol or acetone, to allow better drying of the PMS obtained.

Preparation of the PMS finishes with drying under conditions which allow the removal of the water and/or the washing solvent. Drying can be carried out at temperatures between 80° C. and 400° C. at ambient pressure or under vacuum.

The drying temperature will preferably be between 90° C. and 150° C., and a vacuum of 1 hPa to 100 hPa will preferably be used. The drying process will be carried out under usual conditions known to the person skilled in the art, for example using a rotary drier, quoted here as a non-limiting example.

As a result of the drying process, a porous PMS will be obtained which contains less than about 8%, preferably less than about 5% by weight of water. According to an even better preferred embodiment, a PMS containing about 1% or less by weight of water will be obtained. As mentioned hereinabove, this PMS is insoluble in hydrophilic or hydrophobic organic solvents or in water.

The porous PMS, as obtained by the process described hereinabove, is a fine powder capable of adsorbing a large number of hydrophobic substances. The apparent density of this powder is between approximately 0.04 g/cm$^3$ and 0.8 g/cm$^3$, depending on the method of preparation. It has been established that powders having a density between approximately 0.08 g/cm$^3$ and 0.4 g/cm$^3$ have the best adsorbent capacities, these capacities increasing when the density decreases. The characteristic data of these materials, determined by physical adsorption of nitrogen (carried out on a Sorptomatic 1900 machine manufactured by Carlo Erba) and evaluated on the basis of the Brunauer-Emmett-Teller (BET) equation, were as follows:

specific surface area between 50 m$^2$/g and 500 m$^2$/g, preferably between 75 m$^2$/g and 375 m$^2$/g;
90% of the pores having a radius smaller than 10 angstrom (1 nm), preferably smaller than 9 angstrom (0.9 nm).

In a preferred embodiment, the pore volume of the PMS acccording to the invention is between 0.1 cm$^3$/g and 0.8 cm$^3$/g. It is even better preferred if this volume is between 0.2 cm$^3$/g and 0.7 cm$^3$/g.

In another preferred embodiment, the monolayer volume of the PMS according to the invention is between 10 cm$^3$/g and 60 cm$^3$/g, and it is even better Preferred if this volume is between 15 cm$^3$/g and 50 cm$^3$/g.

Furthermore, the average particle size of the PMS (which, of course, varies depending on the method of preparation) is between 1 $\mu$m and 200 $\mu$m, measured by laser diffraction in powder and in suspension in water in the presence of a surfactant. The surfactant can be e.g. polyoxyethylene (20) sorbitan monooleate, sold under the name of Tween® 80 (origin: ICI, England).

Thermogravimetric measurements have shown that the porous PMS according to the invention is thermally stable up to a temperature of approximately 400° C. or slightly above. Beyond that, chemical conversions take place and, at approximately 500° C., the PMS loses its methyl groups and is converted to silica. FIG. 1 shows the result of differential calorimetry carried out on the PMS according to the invention under the conditions indicated, which illustrates well the thermal behaviour of the polymethylsilsesquioxane according to the invention.

Another feature of the PMS according to the invention is its essentially amorphous nature. FIG. 2 shows the two adsorption bands (halos) centred around 10° and 22° theta and obtained by X-ray diffraction. These two aforementioned bands are typical of the PMS according to the invention and demonstrate that the PMS is an amorphous powder with a low degree of crystallinity.

Lastly, the PMS according to the invention is in the form of conglomerates of nanoparticles of a porous nature and with particle sizes between approximately 1 $\mu$m and 200 $\mu$m. A particle size between approximately 2 $\mu$m and 50 $\mu$m is preferred. This size varies according to the preparation conditions.

A remarkable feature of the PMS according to the invention is its hydrophobic nature, manifested by the fact that the PMS floats on water and remains entirely dry. In contrast, owing to its lipophilic nature, the PMS according to the invention associates itself intimately with any organic molecule and is capable of adsorbing more than five times its own weight in organic substance, as will be shown in the following examples.

Owing to this lipophilicity, its specific surface area and its high pore volume, the PMS according to the invention lends itself to multiple applications as a solid support for a wide variety of materials used in chemistry, perfumery and/or cosmetics.

Among the large number of possible applications, the use of the PMS as a solid support for enzymes has proved highly advantageous. Enzymes fixed to a solid support such as silica, clays or polyolefins are currently used in the pharmaceutical or flavour industries, to quote just two examples. The immobilisation of the enzyme faciltates the separation thereof from the reaction medium and often increases the conversion of the substrate relative to the use of the same, non-immobilised enzyme. Thus the PMS according to the invention can advantageously replace the supports known in the field of enzyme immobilisation.

Non-limiting examples of enzymes which can be fixed to the PMS according to the invention are the lipases, peroxidases, hydrogenases, lyases, proteases and isomerases.

For its use as an enzyme support, the PMS can be used as it is or undergo a treatment which facilitates fixing of the enzyme, for example thermal, acid or basic treatment, or modification of its surface by organosiloxanes. The modifications that can be made to a support to achieve good enzyme immobilisation are known to the person skilled in the art.

A specific example of a reaction in which the PMS according to the invention is used as an enzyme support is the optical resolution of a mixture of enantiomers of an ester or an alcohol. In the case of an ester, this term is taken to mean the hydrolysis or enantioselective transesterification, i.e. of a single enantiomer, of a fixture enantiomers of a chiral ester. In the case of an alcohol, this term signifies the enantioselective esterification of a mixture of enantiomers of a chiral alcohol. The enzyme which will generally be used in this resolution reaction is a lipase, examples of which are *Candida antarctica, Pseudomonas fluorescens, Pseudomonas amano, Humicola lang, Candida cylindracea, Mucor miehei, Chromabacterium viscosum, Aspergillus niger, Mucor javanicus* and *Rhisopus arrhizus.*

The PMS according to the invention can also be used as a support for transition metals or derivatives thereof, thus enabling fixed homogeneous or heterogeneous catalysts to be obtained.

Another application of the PMS according to the invention, which is appropriate to quote here, is the use as a solid receiver for active substances such as perfumes, flavours, insect repellents or anti-microbial agents, e.g. with the aim of obtaining a lasting effect of these substances owing to the slow restitution of these active substances in air or water. For example, the PMS according to the invention, containing odoriferous compounds adsorbed on its surface, can be used in air fresheners.

Another example is the use of the PMS in soaps as a support for perfumes incorporated into the soaps. We were able to ascertain that the smell diffused by soaps containing the PMS is preferred to that of the soap not containing the PMS. The presence of the PMS permits a lasting effect of the perfume, and often the process of deterioration of the perfume owing to the acid or basic media in the soaps is slowed down.

Further applications of this type include shampoos and other hair products, such as conditioners, lacquers and dry shampoos, and also "leave-on" products, that is to say hair cleansing and hair treatment products which stay in the hair after application. Indeed, we ascertained that the PMS was a very effective support for the perfumes intended to be incorporated into these hair-care products, the perfume being released in a controlled and more lasting manner than when used just as it was, i.e. not supported on the PMS.

The concentrations in which the PMS can be used in these applications can vary within a fairly wide range of values. Concentrations in the order of 0.05% to 0.5% by weight, relative to the weight of the product into which it is incorporated, can be quoted as an example. Naturally, this concentration depends on the quantity of perfume added to the product and can easily be adjusted as a function of that quantity.

The PMS has therefore proved highly advantageous as a perfume support in all traditionally perfumed cosmetic, body-care or hair-care applications and also in other applications in functional perfumery, for example detergents or fabric softener.

It can also be used in the extraction of organic substances in solution or suspension in water, as in the case of e.g. fruit juices, infusions of plant substances, wines or other maceration products, or perfumes or perfuming ingredients entrained by water vapour. The adsorbent properties of the PMS according to the invention can also be utilised in the purification of fumes and gases, as in gas masks or cigarette filters, for example.

The PMS has demonstrated great usefulness in non-perfumed soaps, in which it can advantageously adsorb the disagreable odours diffused by bases used in these soaps.

The PMS is also useful in the separation of molecules by chromatography owing to less adsorption of polar substances relative to the polar substances. It has turned out that the PMS according to the invention is particularly well adapted to the separation of molecules by reverse chromatography. For example, we were able to ascertain that it was possible to separate the chlorophyll extract from carotene over a column of the PMS according to the invention by elution with, at the start, a 50:50 mixture of water and methanol and, by increasing the proportion of the methanol, pure methanol, with which complete elution of the colorants is possible. The PMS according to the invention is also suitable for use in steric exclusion chromatography.

Naturally, the applications quoted hereinabove do not constitute an exhaustive list of the potential uses of the PMS according to the invention, and many other applications are possible in which the adsorbent properties of the PMS will advantageously be used.

The invention will now be illustrated by way of the following examples, in which the abbreviations have the usual meaning in the art and the temperatures are given in degrees Celsius.

EXAMPLES

Examples 1 to 4
Preparation of the Polymethylsilsesquioxane (PMS)
1500 g of potassium polymethylsiliconate in solution at 46% in water are diluted with 6000 g of water. Keeping the temperature below 30° C., neutralisation is then carried out with 486 g of acetic acid until reaching pH 7. A white precipitate is immediately formed which is filtered, then washed twice with water. The precipitate is then dried at 120° in an oven under a vacuum of 10 mbar for 12 h. 400 g of dry porous PMS containing 1% of residual water (Karl Fischer analysis) and having a density of 0.08 are obtained. This PMS (referred to as PMS 1) had a specific surface area of 191 $m^2/g$, a pore volume of 0.32 $cm^3/g$ and a volume of the monomolecular layer of 44 $cm^3/g$ (measurements determined by physical adsorption of nitrogen by the BET method). The average particle size was 7 $\mu m$ (measured by laser diffraction).

In order to determine its adsorbent capacity with respect to organic substances, limonene contained in a burette was measured out over 2 g of PMS 1 contained in a rotating groove until the PMS 1 became slightly sticky. The volume run off was then measured: 11 ml, i.e. 5.5 ml of limonene adsorbed per g of PMS 1.

By proceeding as described above for example 1, but by replacing the acetic acid by sulphuric acid at 10% weight (ex. 2), phosphoric acid at 20% (ex. 3) or a stream of carbon dioxide gas (ex. 4), at pH 10 a white precipitate was formed which was filtered, washed twice with water and dried at 120° C. at 10 mbar for 12 h.

The properties of the PMS obtained after drying are set out in table 1 (PMS 1 to 4). It was ascertained that the PMS obtained had different surface areas and different pore volumes and that in all cases they adsorbed more than 3 ml of limonene per g of PMS.

TABLE 1

Comparison of the adsorbent properties of the porous PMS obtained by the methods used in examples 1 to 4

| Example | Acid | Surface area $m^2/g$ | Density | Limonene adsorbed ml/g | Pore volume $cm^3/g$ | Particle size $\mu m$ |
|---|---|---|---|---|---|---|
| 1 | $CH_3CO_2H$ | 191 | 0.08 | 5.5 | 0.32 | 7 |
| 2 | $H_2SO_4$ 10% | 275 | 0.086 | 4 | 0.21 | 15 |
| 3 | $H_3PO_4$ 20% | 300 | 0.09 | 4 | 0.3 | |
| 4 | $CO_2$ | 220 | 0.138 | 3.4 | 0.18 | |

Examples 5 to 9
Extraction of Organic Substances From Water
Solutions or suspensions containing 10 g of organic substance in 1 liter of water were stirred at 20° C. with 5 g of the powdered PMS obtained in example 1 (PMS 1) for 10 minutes. The solid was then filtered and weighed, then the residual aqueous phase, which was extracted with diethyl ether, was weighed. In this way, the quantity of organic substance extracted by the adsorbent in the water is determined.

As shown in table 2, the porous PMS has the remarkable property of very effectively extracting the organic substances from the water. The products having poor solubility, such as toluene (ex. 5) or citral (ex. 6), are completely extracted, whereas the highly soluble substances such as butanol (ex. 7), methyl ethyl ketone (ex. 8) or ethylene glycol diethyl ether (ex. 9) are extracted to at least 70%. As the porous PMS is hydrophobic, it contains only small amounts of water when it is filtered using an organic solvent such as methanol, ethanol, acetone or methylene chloride.

TABLE 2

Percentage of product extracted by 5 g of adsorbent support starting from a solution containing 10 g of organic substance in 1 liter of water

| Examples | Substance adsorbed | Level of extraction |
| --- | --- | --- |
| 5 | Toluene | 100% |
| 6 | Citral | 100% |
| 7 | n-Butanol | 84% |
| 8 | Methyl ethyl ketone | 70% |
| 9 | Ethylene glycol diethyl ether | 75% |

Example 10
Enantioselective Saponification of 2-pentyl-1-cyclopenten-1-yl Acetate Using a Lipase Fixed to a Support Derived From the PMS A. Preparation of the Fixed Lipase A suspension of the polymethylsilsesquioxane according to the invention in a 9:1 mixture of propan-2-ol and $H_2O$ was prepared in a proportion of 5 ml of liquid per g of support. The suspension was stirred for 1 h at 50°. It was then cooled to ambient temperature and stirred for a further 10 h before being diluted in water in a ratio of 1:2. After being stirred for 1 h, the suspension was filtered. The product can be stored moist.

To fix the lipase to this pretreated support, 1 g of an adsorbate of *Pseudomonas fluorescens* on clay (origin: Biocatalysts, Great Britain) was suspended in 4 ml of a phosphate buffer solution at pH 7 and 0°. After being stirred for 1 h, the suspension was filtered and the extract diluted 1:1 with a 1:4 mixture of propan-2-ol and phosphate buffer solution (0.5 M, pH 7, 1 ml) before addition of the support pretreated as described hereinabove (0.5 g to 2 g equivalent based on dry weight). The suspension was stirred at 50° for 15 h before isolation of the immobilised enzyme by filtration, washing with cold acetone and with pentane. The product is air-dried at ambient temperature.

The thus obtained lipase immobilised on the PMS according to the invention can be used just as it is. It can also be used in the preparation of a biocomposite of the lipase-PMS-silicone type. For this purpose, 10 g of the adsorbate obtained as described hereinabove were dispersed in a mixture containing 7 g of polymethyldisiloxane having silanol terminations with high functionality (0.9% to 1.2% functionality; origin: ABCR GmbH, Germany) and 21 g of polymethyldisiloxane having silanol terminations with low functionality (0.1% functionality; origin: ABCR GmbH, Germany).

After addition of a cross-linking agent comprising 12 g of a polydiethylsilicate containing 45% by weight of silica solids (origin: ABCR GmbH & Co., Germany) and 0.6 g of tin 2-ethylhexanoate (origin: ABCR GmbH & Co., Germany), the mixture obtained was poured over aluminium. The gelation time in air and at ambient temperature was approximately 30 mins, the maturing time approximately 1 h to 2 h. An elastic material was obtained which, after grinding, is used in the enantioselective hydrolysis reaction as described hereinbelow.

B. Saponification Reaction 0.4 g of a racemic mixture of 2-pentyl-1-cyclopenten-1-yl acetate (obtained as described e.g. in European application EP-A-841 331 in the name of Firmenich S A) in the form of a suspension in a mixture containing 0.2 g of ethanol, 0.2 g of isopropanol and 0.1 g of a triethanolamine buffer solution at pH 7.5 was hydrolysed using 50 mg of immobilised *Pseudomonas fluorescens*, obtained by the two methods of preparation described under A and corresponding to approximately 15 g of enzyme. The temperature was maintained at 25° for a reaction time of 40 h. The mixture was then extracted with methyl-tert-butyl ether. The extract was analysed by gas chromatography in a 25 m long Megadex 5 chiral column (100° to 150° at 3°/min). An enantiomeric excess (ee) of approximately 93% and conversion of almost 100% was obtained.

Example 11
Use of the PMS Containing Adsorbed Perfume in Body-Care Products

A. Baby Powder 0.3 g of the PMS obtained in example 1 was mixed with 0.5 g of a standard perfuming base in order to obtain a dry powder. This was mixed with 95.7 g of sterilised talc (cosmetic quality) and 3.5 g of micronised zinc oxide. The product thus obtained was then screened in order to eliminate agglomerates and obtain a baby powder of the desired quality.

B. Powdered Deodorant 1.0 g of the PMS obtained in example 1 was mixed with 1.5 g of a standard perfuming base. The dry powder which forms was mixed with 97.0 g of sterilised talc and 0.5 g of Triclosan (e.g. the product Irgasan® DP-300 made by Ciba SC, Basle, Switzerland). A powder was thus obtained which is suitable as a perfumed deodorant.

Example 12
Preparation of a Perfumed Composition for an Air Freshener

A perfumed composition for an air freshener was prepared from the following ingredients:

| | Ingredients | % by weight |
| --- | --- | --- |
| I. | Dolomite | 5.0 |
| | PMS | 2.0 |
| | Perfume | 13.0 |
| | Tween ® 20[1] | 0.2 |
| II. | Water | 49.4 |
| | Tylose MHB 30,000[2] | 0.4 |
| III. | Plaster (moulded) | 30.0 |
| | Total | 100.0 |

[1] polyoxyethylene sorbitan monolaurate; origin: ICI, Great Britain
[2] carboxymethyl cellulose; origin: Hoechst AG, Germany Parts I and II were thoroughly mixed separately and then together. The mixture thus obtained was poured into plaster moulds prepared beforehand in various decorative shapes.

Example 13

Preparation of Perfumed Compositions for Air Fresheners

Perfumed compositions for air freshening gels were prepared from the following ingredients:

| | Ingredients | Compositions A | B |
|---|---|---|---|
| | | % by weight | |
| I. | Satiagel K6[1] | 1.3 | 1.3 |
| | Glycerin | 3.0 | 3.0 |
| | Water | 87.4 | 86.4 |
| | Glydant II[2] | 0.1 | 0.1 |
| | Tylose MHB 30,000[3] | 0.2 | 0.2 |
| II. | Magnesium carbonate | — | 2.5 |
| | SiO$_2$ | 3.0 | 1.5 |
| | Perfume | 5.0 | 5.0 |
| | Total | 100.0 | 100.0 |

[1] carrageenan; origin: Kelco Int. Ltd., USA
[2] preservative; origin: Lonza Ind., Switzerland
[3] see example 12

Parts I and II were thoroughly mixed separately. After heating part I to 75° C., part II was added to it and the whole was thoroughly mixed to obtain a homogeneous mixture. The compositions thus obtained were then moulded into various shapes in a known manner to produce air freshening products.

Example 14

Preparation of Non-Perfumed Soaps Containing the PMS

A soap with a non-synthetic base was prepared from the following ingredients:

| Ingredients | % by weight |
|---|---|
| Sodium salt of tallow fatty acid or another natural fatty acid* | 88.95 |
| Water | 10.00 |
| Sodium chloride | 0.50 |
| Glycerin | 0.50 |
| Free alkali | 0.05 (or free fatty acids 0.5%–1.0%) |
| Total | 100.00 |

*palm, palm stearine, olive, etc.

Soaps were then prepared without any additives and with the addition of 1.5% by weight of the PMS, with this base having a strongly disagreeable odour. After preparation, a panel of appraisers did not notice any difference between these two soaps. The soaps were then stored at 40° for 30 days, after which the panel greatly preferred the soap containing the PMS owing to a reduced level of odour. The result was confirmed by the same panel which appraised the odour of these soaps again after further storage for two months at ambient temperature. All the appraisals were carried out blind.

Example 15

Preparation of a Leave-On Conditioner

A leave-on conditioner, i.e. one not intended to be rinsed off, was prepared from the following ingredients:

| | Ingredients | % by weight |
|---|---|---|
| A) | Phytantriol ®[1] | 0.10 |
| | Renex ® 690[2] | 0.20 |
| | Propylene glycol | 1.00 |
| | D-Panthenol[1] | 0.20 |
| | Deionised water | 94.85 |
| | Ethoquad ® O/12[3] | 0.70 |
| | Crosilk liquid[4] | 0.05 |
| | Mackpro NSP[5] | 0.10 |
| | Arginine hydrochloride | 0.10 |
| | Kathon ® CG[6] | 0.05 |
| | Glydant ®[7] | 0.20 |
| | Germall II[8] | 0.20 |
| | Sodium phosphate, tribasic (12H20) | 0.25 |
| | Phosphoric acid (aqueous solution at 42%) | 0.40 |
| | Dow Corning 929 cationic emulsion[9] | 1.00 |
| B) | PMS[10] | 0.30 |
| | Perfume[10] | 0.30 |
| | Total | 100.00 |

[1] Origin: Hoffmann-La Roche
[2] Nonoxynol-10; origin: ICI Surfactants
[3] Isopropyl alcohol (and) PEG-2 oleammonium chloride; origin: Akzo Nobel
[4] Silk powder; origin: Croda
[5] Quarternium-79 hydrolysed silk; origin: McIntyre
[6] Methylchloroisothiazoline and methylisothiazoline; origin: Rohm & Haas
[7] DMDM hydantoin; origin: Lonza
[8] Diazolidinyl Urea; origin: ISP
[9] Amodimethicone (and) Nonoxynol-10 (and) Tallowtrimonium Chloride; origin: Dow Corning
[10] Origin: Firmenich SA The Phytanthiol® was mixed thoroughly with the Renex® 690, and the other Ingredients from part A were added. Next, the PMS according to the invention was thoroughly mixed with the perfume and left overnight for complete absorption of the perfume. Part B thus prepared was added to part A and the whole was thoroughly homogenised, thereby producing a conditioner to be shaken before use and intended to be applied to wet hair without subsequent rinsing.

Alternatively, a thickener can also be added to this product to prevent separation of the particles of perfumed PMS.

If necessary, the pH is adjusted to 4–4.5 using phosphoric acid.

When this product was applied to the hair and compared in a blind test with a similar product, but containing the perfume without being supported on the PMS, it was ascertained that the hair treated with the former released the fragrance of the perfume for much longer than when the conventionally perfumed conditioner was used.

Example 16

Preparation of Shampoos

A liquid shampoo was prepared from the following ingredients:

| Ingredients | % by weight |
|---|---|
| Deionised water | 64.38 |
| Kathon ®[1] CG | 0.10 |
| Comperlan ®[2] KD | 1.50 |
| Texapon ®[3] NSO IS | 32.00 |
| Citric acid | 0.02 |
| Perfume[4] | 0.50 |
| Sodium chloride | 1.50 |
| Total | 100.00 |

The ingredients were thoroughly mixed in order to obtain a homogeneous shampoo base from which the following compositions were prepared:

| Composition | Ingredients |
|---|---|
| A | Base + 0.5% by weight of PMS |
| B | Base + 0.5% by weight of Luviquat Hold[5] |
| C | Base + 0.5% of Luviquat Hold[5] + 0.5% PMS |
| D | Base + 0.5% of Jaguar Exel[6] |
| E | Base + 0.5% of Jaguar Exel[6] + 0.5% PMS |

[1] see example 15
[2] cocamide DEA; origin: Henkel
[3] sodium laureth sulphate; origin: Henkel
[4] origin: Firmenich SA
[5] cationic polymer; origin: BASF
[6] cationic polymer; origin: Rhodia In the preparation of compositions C and E, the perfume was first mixed with the PMS, as described in the preceding example, before incorporation of this mixture into the base. Compositions A and E were compared blind by a panel of appraisers who were asked to assign a value, on a rising scale from 1 to 10, corresponding to the intensity of the fragrance perceived on wet and dry hair.

The results of these appraisals are summarised in the following table:

| Composition | Intensity of the fragrance |
|---|---|
| BASE | 3 |
| A | 6 |
| B | 5 |
| C | 6 |
| D | 6 |
| E | 8 |

It is clearly apparent from this table that, when the perfume is added to the shampoo on a PMS support according to the invention, the latter distinctly improves the deposition of the perfume on the hair. Furthermore, it was ascertained that the hair remained perfumed for longer than when the perfume was added just as it was to the shampoo base.

Example 17

Preparation of a Conditioner to be Rinsed Off

A conditioner to be rinsed off was prepared from the following ingredients:

| | Ingredients | % by weight |
|---|---|---|
| A) | Deionised water | 91.60 |
| | Aqueous solution at 20% of chlorhexidine digluconate[1] | 0.25 |
| | Nipagin ® MNa[2] | 0.10 |
| | Nicotinamide[3] 98% | 0.05 |
| | Genamin ® KSL[4] | 3.00 |
| | Lactic acid L(+) 85%–90% | 0.30 |
| | D-Panthenol[5] | 0.30 |
| | Dow Corning Q2-5200[6] | 0.20 |
| | Ethyl alcohol | 1.30 |
| | Lanoline Ultra[7] | 0.20 |
| B) | Jaguar C-162[8] | 1.00 |
| | Natrosol 250 H[9] | 0.70 |
| C) | PMS[10] | 0.50 |
| | Perfume[10] | 0.50 |
| | Total | 100.00 |

[1] origin: ICN Biochemicals
[2] Sodium methylparaben; origin: NIPA
[3] Niacinamide; origin: Acros Organics
[4] PEG-5 Stearyl Ammonium Lactate; origin: Clariant
[5] origin: Hoffmann-La Roche
[6] Laurylmethicone Copolyol; origin: Dow Corning
[7] origin: Westbrook Lanolin
[8] Hydroxypropyl Guar Hydroxypropyltrimonium Chloride; origin: Rhone-Poulenc
[9] Hydroxyethyl cellulose; origin: Hercules
[10] origin: Firmenich SA Part A was heated to approximately 60° C. until complete solution of the cetyl alcohol. Part B, which had been mixed beforehand, was then added. Homogenisation was then carried out until the cream thus formed had cooled to ambient temperature.

The PMS was thoroughly mixed with the perfume, and the mixture was all wed to rest overnight for good absorption. This perfumed PMS was then added to the previously prepared cream to obtain the desired conditioner. The pH of the latter can be adjusted to around 4 if necessary, using lactic acid.

What is claimed is:

1. A porous polymethylsilsesquioxane in powdered form containing the units $$\left[ \begin{array}{c} CH_3 \\ | \\ CH_3-Si-O- \\ | \\ CH_3 \end{array} \right] \quad \text{and} \quad \left[ \begin{array}{c} | \\ O \\ | \\ -O-Si-O- \\ | \\ CH_3 \end{array} \right]$$

chain ends                    Units of the material and having a specific surface area between approximately 50 m$^2$/g and 500 m$^2$/g and a pore radius smaller than 1 nm for 90% of the pores, wherein the polymethylsilsesquioxane is insoluble in water and organic solvents.

2. A polymethylsilsesquioxane according to claim 1, having a pore volume between approximately 0.1 cm$^3$/g and 0.8 cm$^3$/g.

3. A polymethylsilsesquioxane according to claim 1, having a monolayer volume between approximately 10 cm$^3$/g and 60 cm$^3$/g.

4. A polymethylsilsesquioxane according to claim 1, having two adsorption bands around 10° and 22° obtained by X-ray diffraction.

5. A polymethylsilsesquioxane according to claim 1, having an average particle size between 1 μm and 200 μm.

6. A polymethylsilsesquioxane according to claim 1, having thermal stability up to approximately 400° C. and a decomposition temperature of approximately 500° C., as determined by differential calorimetry and thermogravimetry.

7. A polymethylsilsesquioxane according to claim 1, having a powder density between approximately 0.04 g/cm$^3$ and 0.8 g/cm$^3$.

8. A polymethylsilsesquioxane according to claim 1, in the form of a conglomerate of porous nanoparticles having a particle size between approximately 1 μm and 200 μm.

9. A polymethylsilsesquioxane according to claim 1, which also contains the units

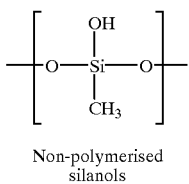

Non-polymerised silanols

10. A polymethylsilsesquioxane according to claim 1, having a specific surface area between approximately 75 m$^2$/g and 375 m$^2$/g, a pore volume between approximately 0.2 cm$^3$/g and 0.7 cm$^3$/g, a monolayer volume between approximately 15 cm$^3$/g and 50 cm$^3$/g and a pore radius smaller than 0.9 nm for 90% of the pores.

11. A polymethylsilsesquioxane according to claim 1, containing odoriferous compounds.

12. A polymethylsilsesquioxane according to claim 11, included in an air freshener, soap, shampoo or other hair-care product, a bath or shower gel, a conditioner, a lacquer, a cosmetic composition, a detergent or fabric softener.

13. A process for the preparation of a porous polymethylsilsesquioxane in powdered form, the process comprising the precipitation, by means of an acid, of an aqueous solution containing a polymethylsiliconate of the general formula

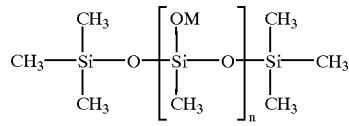 (I)

in which n is a whole number between approximately 20 and 100 and M is an alkaline metal or alkaline-earth metal or NH$_4^+$.

14. A process according to claim 13, wherein the acid is added to the solution until a pH of about at least 11 is reached.

15. A process according to claim 13, wherein the acid is added to the solution until a pH of about at least 7 is reached.

16. A process according to claim 13, wherein M is sodium or potassium.

17. A process according to claim 13, wherein the acid is sulphuric acid, phosphoric acid or acetic acid.

18. A process according to claim 13, wherein the polymethylsilsesquioxane is isolated from the solution and washed and dried at temperatures between approximately 80° C. and 400° C.

19. A process according to claim 13, wherein the polymethylsiliconate of the formula (I) is prepared from a polymethylhydrosiloxane of the general formula

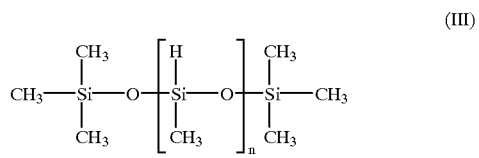 (III)

in which n is a whole number between 20 and 100.

20. A process according to claim 19, wherein the polymethylsiliconate is prepared by scission of the Si—H bond by means of an aqueous base or by reaction with a carbonyl substrate catalyzed by a suitable metal-containing catalyst followed by hydrolysis.

21. A porous polymethylsilsesquioxane in powdered form obtainable by the process of claim 13.

* * * * *